United States Patent
Mo

(10) Patent No.: US 9,375,200 B2
(45) Date of Patent: Jun. 28, 2016

(54) ULTRASOUND TRANSDUCER WITH DIFFERENTIAL MODE SIGNALING

(71) Applicant: Jian-Hua Mo, Palo Alto, CA (US)

(72) Inventor: Jian-Hua Mo, Palo Alto, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 593 days.

(21) Appl. No.: 13/797,489

(22) Filed: Mar. 12, 2013

(65) Prior Publication Data

US 2014/0269206 A1    Sep. 18, 2014

(51) Int. Cl.
| | |
|---|---|
| H04R 1/32 | (2006.01) |
| A61B 8/00 | (2006.01) |
| A61B 8/12 | (2006.01) |
| G10K 11/34 | (2006.01) |

(52) U.S. Cl.
CPC ... *A61B 8/56* (2013.01); *A61B 8/12* (2013.01); *A61B 8/4483* (2013.01); *G10K 11/341* (2013.01); *A61B 8/445* (2013.01); *A61B 8/4488* (2013.01)

(58) Field of Classification Search
CPC .......... A61B 8/12; A61B 8/56; A61B 8/445; A61B 8/4483; A61B 8/4488; G10K 11/341; H04R 1/32
See application file for complete search history.

(56) References Cited

U.S. PATENT DOCUMENTS

| | | | |
|---|---|---|---|
| 6,229,247 B1 * | 5/2001 | Bishop | H01L 41/107 310/328 |
| 6,695,785 B2 * | 2/2004 | Brisken | A61B 8/12 600/459 |
| 6,918,877 B2 | 7/2005 | Hossack et al. | |
| 7,955,139 B2 | 6/2011 | Straka et al. | |
| 8,144,807 B2 | 3/2012 | Mirfakhraei et al. | |
| 9,131,917 B2 * | 9/2015 | Telfort | A61B 5/6843 |
| 2002/0099292 A1 * | 7/2002 | Brisken | A61B 8/12 600/466 |
| 2005/0061536 A1 | 3/2005 | Proulx | |
| 2006/0142659 A1 * | 6/2006 | Okazaki | B06B 1/0622 600/459 |
| 2007/0038032 A1 | 2/2007 | De Canniere et al. | |
| 2008/0042519 A1 | 2/2008 | Marshall et al. | |
| 2014/0269206 A1 * | 9/2014 | Mo | A61B 8/12 367/138 |

* cited by examiner

*Primary Examiner* — Daniel Pihulic

(57) ABSTRACT

Rather than using a coaxial cable, a twisted pair of wires is provided for each element-to-beamformer connection. Differential mode signals are transmitted between the transducer element and the respective channel. A multi-layer element is used for operation with the differential mode signals. In catheters or other probes, coaxial cables are not used. Using differential mode signals over twisted pairs allows reduction or rejection of common mode cross-talk and/or interference.

16 Claims, 2 Drawing Sheets

ULTRASOUND TRANSDUCER WITH DIFFERENTIAL MODE SIGNALING

BACKGROUND

The present embodiments relate to ultrasound transducers. In particular, the present embodiments relate to front-end operation of an ultrasound system.

On the front end of ultrasound systems, a transmit beamformer generates high voltage transmit waveforms and transmits the transmit waveforms to a transducer. Transmit waveforms are provided for different elements of the transducer. For receive operation, the transducer transmits low voltage signals to a receive beamformer. The transmit and receive beamformer channels are typically connected to the elements of the transducer with coaxial cables. The coaxial cables shield the transmit and receive waveforms from crosstalk and other interference.

Ultrasound transducers may be positioned in cardiac catheters. Due to tight space inside the catheter body and the large number elements of the transducer, fully shielded coax cables may not be used to connect the beamformer channels to the elements. Non-coaxial signal wires, such as traces on flex circuit material, are used, resulting in higher level inter-channel cross-talk and higher susceptibility to external noise interference. As a result, images with this catheter construction exhibit centerline noise artifacts, degrading image quality at times, especially for 3D images.

BRIEF SUMMARY

By way of introduction, the preferred embodiments described below include methods and systems for ultrasound transducer element systems. Rather than using a coaxial cable, a twisted pair of wires is provided for each element-to-beamformer connection. Differential mode signals are transmitted between the transducer element and the respective system channel. A multi-layer element is used for operation with the differential mode signals. In catheters or other probes, coaxial cables are not used for at least part of the path between element and system channel. Using differential mode signals over twisted pairs allows reduction or rejection of common mode cross-talk and/or interference.

In a first aspect, an ultrasound transducer element system is provided. At least one ultrasound transducer element has at least first and second layers of transducer material. A first electrode is between the first and second layers. The electrode connects to ground for transducing. A second electrode is adjacent the first layer and not the second layer, and a third electrode is adjacent the second layer and not the first layer. A twisted pair of wires has a first wire of the pair connected with the second electrode and a second wire of the pair connected with the third electrode. A first beamformer channel connects with the twisted pair. The first beamformer channel is operable with differential mode signals corresponding to the second and third electrodes.

In a second aspect, an ultrasound transducer element system is provided. At least one ultrasound transducer element includes at least first and second layers of transducer material. A system channel is configured to operate with differential mode signals. A twisted pair connects the system channel to the ultrasound transducer element.

In a third aspect, a method is provided for noise and cross-talk reduction in ultrasound imaging. Differential mode signals are transmitted between an ultrasound transducer and a beamformer. The differential mode signals are combined.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

An ultrasound array design uses differential mode signals to reduce inter-channel crosstalk and external noise interference. Twisted pair wires provide for effective reduction of inter-channel crosstalk and external noise interference, while still maintaining the tight space requirement due to catheter body size. The use of twisted pair wires may save space for the catheter body design and may be a cost effective alternative to coax cables. For disposable catheter devices, twisted pairs may be more economical. In other embodiments, the differential mode signals over twisted pair is provided in non-catheter probes, such as transesophageal (TEE), intercavity, handheld, or other ultrasound probes.

Figure 1:
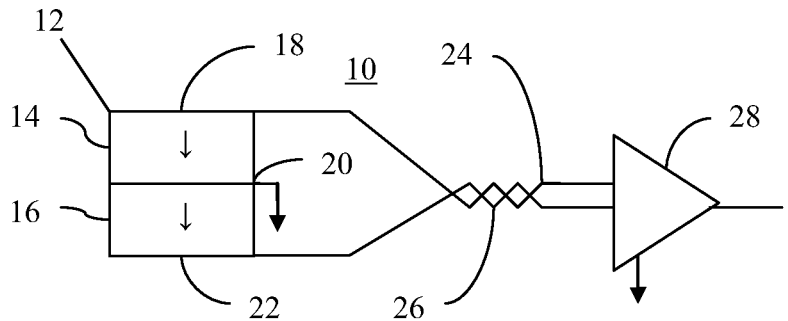
FIG. 1 is a circuit diagram of a first embodiment of a multi-layer element transducer system with a twisted pair of wires.
Figure 2:
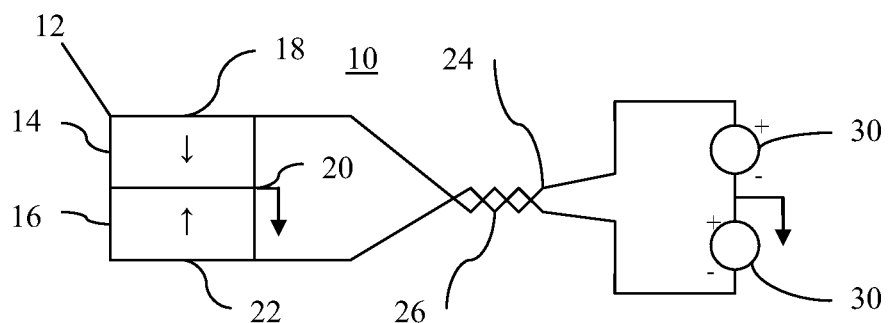
FIG. 2 is a circuit diagram of a second embodiment of a multi-layer element transducer system with a twisted pair of wires.
Figure 3:
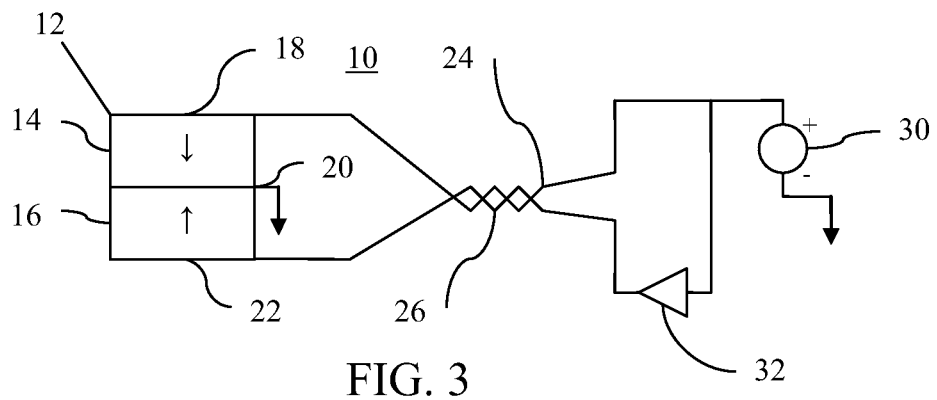
FIG. 3 is a circuit diagram of a third embodiment of a multi-layer element transducer system with a twisted pair of wires.

FIGS. 1-3 shows different embodiments of an ultrasound transducer element system 10. In general, the system 10 includes a transducer element 12, a system channel 24, and a twisted pair 26 of wires. FIGS. 1-3 show different system channel 24 arrangements and different transducer material poling. Three possible arrangements are shown, but other combinations using the same or different poling and/or system channels may be used. Additional, different or fewer components may be provided. For example, FIGS. 1-3 show one element 12, one twisted pair 26 and one system channel 24, but additional elements 12, respective twisted pairs 26, and respective system channels 24 may be provided for operation of an array transducer. Macro-elements, multiplexing, or other functions may result in a lack of one-to-one correspondence between elements 12, twisted pairs 26, and/or system channels 24.

The transducer element 12 has a top layer 14 and a bottom layer 16 of piezoelectric or other material. Each layer is capable, with electrodes 18, 20, and 22, of transducing between electrical and acoustic energies. The layers 14, 16 may both be between a backing layer and a matching layer. Additional layers 14, 16 of transducer material may be provided, such as three or more layers. The layers 14, 16 are stacked along a range dimension or direction of propagation. Each layer 14, 16 has the same or different elevation and azimuth extent and shape, but may have different shapes and/or extents.

The layers 14 and 16 are a same or different piezoelectric material, such as a piezoelectric single crystal, piezoelectric ceramic or piezoelectric polymer material, or their composites with epoxy or other filler materials. In alternative embodiments, the one or more of the layers 14, 16 are electrostatic micromachined devices, such as electrostatic moving membrane devices. In yet other embodiments, the one or more of the layers 14, 16 are electrostrictive material, such as PMN-PT. Each of the layers 14, 16 has a same or different geometry and/or material. For example, the same thickness is used for each layer, such as a ½ mm thickness. Other thicknesses may be used, including thicknesses that vary in one or more dimensions.

In one embodiment, the top and bottom layers 14, 16 have different transducer materials. For example, the bottom layer 16 is a solid piezoelectric material, such as a solid ceramic or electrostatic substrate. The solid piezoelectric material is free of epoxy or free from kerfs within each transducer element 12. The top layer 14 is piezo-composite material, such as a combination of piezoelectric ceramic and epoxy or polymer. Piezo-composite materials include piezoelectric material beams separated by epoxy-filled kerfs in one dimension or piezoelectric material posts separated by epoxy-filled kerfs in two dimensions, but other piezo-composites may be used. In one example embodiment, the top layer 14 is a piezo-composite having an acoustic impedance of 14-19 Mrayl, and the bottom layer 16 is a solid piezoelectric material having an acoustic impedance of about 30 Mrayl. Alternatively, the top and bottom layers 14, 16 are of the same material, size, and shape.

The transducer material of the layers 14, 16 is poled. The poling is along or substantially parallel to the propagation direction (e.g., along the thickness or range direction). In one embodiment, the different layers have substantially opposite poling directions ("bidirectional poling"). FIGS. 2 and 3 show examples of opposite poling as represented by the arrows in the layers 14, 16. The reverse of the poling shown in FIGS. 2 and 3 may be used. In other embodiments, two or more layers 14, 16 are poled in a same direction ("unidirectional poling"). FIG. 1 shows an example of poling in the same direction as represented by the arrows in layers 14, 16. The direction of the poling for both layers 14, 16 may be reversed. Opposite (bidirectional) poling may be used in the embodiments of FIG. 1, and poling in a same direction (unidirectional) may be used in the embodiments of FIG. 2 or 3.

The poling determines the frequency of resonance. When transmitting and receiving differential mode signals, the element 12 operates in a low frequency fundamental mode ($F_0$) when poling is "unidirectional" and in high frequency fundamental mode ($2F_0$) when poling is "bidirectional."

The layers 14, 16 of transducer material are separated by an electrode 20. The electrode 20 is connected with a system or other ground. The connection is direct, but may be through a capacitor. In alternative embodiments, the connection is switchable. A passive or active switch connects the electrode 20 to ground. During transmit, receive, or both transmit and receive operation, the electrode 20 is connected with ground or a fixed potential, providing a ground electrode for operation with differential mode signals.

Each layer 14, 16 of transducer material is sandwiched between a pair of electrodes 18, 20, 22. The top layer 14 has electrodes 18, 20 on opposite sides. The bottom electrode 22 is not adjacent to the top layer 14. The bottom layer 16 has electrodes 20, 22 on opposite sides. The top electrode 18 is not adjacent to the bottom layer 16. The center electrode 20 is a single electrode shared by both layers 14, 16. Alternatively, the center electrode 20 is formed from two electrodes in contact with each other. The electrodes 18, 20, 22 are stacked with the layers 14, 16 in the range or thickness dimension. The electrodes 18, 20, 22 have the same elevation and azimuth extent as the layers 14, 16, but may have a greater or lesser extent and/or different shape. A difference in potential between the electrodes 18, 20 and 20, 22 on opposite sides of a given layer 14, 16 is used for transduction in the layer 14, 16.

The electrodes 18, 20, 22 are metal, but other conductors may be used. Sheets with or without flexible circuit material (e.g., polyester film) form the electrodes 18, 20, 22. Alternatively, the electrodes 18, 20, 22 are deposited material. The electrodes 18, 20, 22 are formed as part of the stack, such as with sintering, or are separate layers, such as with asperity contact. In one embodiment, the center electrode 20 is formed in the stack by sintering or asperity contact, but the outer electrodes 18, 22 are formed in the stack with asperity contact and bonding.

The top electrode 18 is a positive lead, but may be a negative lead. The bottom electrode 22 is a negative lead, but may be a positive lead. The ground lead of the middle electrode 20 is common to both layers 14, 16. Differential mode signals use the positive and negative leads for an element. Two signals or waveforms are provided from and/or to the element 12 for operation with differential mode signaling using the signal electrodes 18, 22.

The positive and negative leads connect to the twisted pair 26 of wires. The same connection is used for each system channel 24 and corresponding element 12. The electrodes 18, 22 connect with wires, traces, or other conductors for routing signals to or from the electrodes 18, 22. In one embodiment, traces on flex circuit material connect the twisted pair 26 to the electrodes 18, 20 near the element 12, such as within millimeters or centimeters. One or both of the electrodes 18, 22 have a fixed or non-switched connection. Alternatively, one or both of the connections of the electrodes 18, 22 are switched, such as with passive and/or active switching.

The twisted pair 26 of wires has two wires twisted together in a helix or other arrangement. Any number of twists, turn frequency, variation in twist along the length, or other characteristic of twisted pairs may be used. The wires are insulated from each other. In one embodiment, the insulation is joined so that the wires of the twisted pair are connected together while being electrically isolated from each other. In other embodiments, the wires of a pair are not joined. In yet another embodiment, an outer sheaf or cover is provided over the shielded, twisted pair.

One wire of the twisted pair 26 connects to the top electrode 18, and the other wire of the twisted pair 26 connects to the bottom electrode 22. The wires of the twisted pair 26 electrically connect to the top and bottom electrodes 18, 22 on sides of the layers 14, 16 opposite to the ground electrode 20.

The twisted pair 26 is used instead of coaxial cables for transmitting signals. Twisted pairs do not require the ground shielding of coaxial cables, may take up less space, and may be more cost effective. The twisted pair 26 operating with differential mode signals may provide effective immunity to crosstalk and noise interference.

Both wires connect with the system channel 24. At least part of the system channel 24 includes wires or traces for differential operation. The system channel 24 is configured by hardware, firmware, and/or software to operate with differential mode signals. In one embodiment, the system channel 24 is one or more beamformer channels connected with the twisted pair 26. The beamformer channel operates with differential mode signals by generating differential mode signals and/or by combining the differential mode signals for common mode rejection.

The system channel 24 is a transmit channel, receive channel, signal path, or combinations thereof. In one embodiment, the system channel 24 includes a transmit/receive (T/R) switch. The T/R switch is a passive, active or both passive and active switching circuit. The T/R switch routes low voltage signals to the receive beamformer channel and routes higher voltage signals from a transmit beamformer channel while protecting or open circuiting the receive beamformer channel. The T/R switch circuit connects the twisted pair 26 with the system channel 24. Parts of the system channel 24, such as a differential amplifier and/or inverter, are positioned on either side of the T/R switch.

In one embodiment, the system channel 24 is configured to generate differential mode signals for transmit operation. The transmit waveform is generated with a copy of the same amplitude, but 180 degrees out of phase. Two transmit waveforms with the same amplitude but opposite polarity are generated for applying to the different layers 14, 16 via the top and bottom electrodes 18, 22 at a same time. Waveforms of different amplitudes and/or other than 180 degree phase shift may be used.

One of the transmit waveforms is applied to the positive lead, and the other transmit waveform is applied to the negative lead. Because the transmit signals going through twisted pair 26 are of opposite polarity and equal amplitude, crosstalk to other channels may be reduced or cancelled out.

As a transmit beamformer channel, the system channel 24 is an analog or digital transmit beamformer channel. For example, envelope samples are used to construct the transmit waveform as a sinusoid. Other sources of waveforms may be used, such as waveform generators, pulsers, switches, a waveform memory, mixer, or digital-to-analog converter. The waveform for a given transmit beamformer channel is delayed and amplified relative to other transmit beamformer channels.

FIGS. 2 and 3 show two example configurations for a transmit beamformer to generate differential mode signals. In the example of FIG. 2, two waveform generators 30 create the differential mode transmit signals. For example, two different transmit beamformer channels form the system channel 24 to create the opposite polarity signals for the one element 12. Each transmit beamformer channel provides one of the differential mode signals. Each transmit beamformer channel connects with a respective one of the wires of the twisted pair 26.

In the example of FIG. 3, only one waveform generator 30 (e.g., transmit beamformer channel) is used. An inverter 32 connects with the output of the waveform generator 30. The inverter 32 creates a copy of the transmit waveform, but with opposite polarity. The output of the generator 30 connects with one wire of the twisted pair 26 and the inverter 32. A splitter, such as a connection, is provided to route the transmit waveform along different paths. The output of the inverter 32 connects with another one of the wires of the twisted pair 26. A delay or other device may be provided to account for any delay introduced by the inverter 32 in the connection without the inverter 32.

The differential mode transmit waveforms generated by the system channel 24 are provided through the twisted pair 26 to the element 12. Since the middle electrode 20 is grounded during transmit operation, the layers 14, 16 generate acoustic energy based on the relative differential mode signal applied to that layer 14, 16. As a result, common mode information cancels out, leaving acoustic energy generated by the difference in the differential mode signals.

As a receive beamformer channel, the system channel 24 is configured by hardware, firmware, and/or software to remove common mode information from signals of the first and second layers 14, 16 provided over the twisted pair 26. The wires of the twisted pair 26 connect with the receive beamformer channel. The receive beamformer channel receives the differential mode signals and combines the signals, rejecting or reducing common mode information.

FIG. 1 shows one example of part of the receive beamformer channel. A differential amplifier 28 has a positive input connected to one of the wires of the twisted pair 26 and a negative input connected to another one of the wires of the twisted pair 26. The differential amplifier 28 is a preamplifier, but may be any circuit or transistor configuration for performing a differencing function. The differential amplifier 28 takes the difference of the signals on the paired wires (i.e., difference of the differential mode signals).

External noise interference from other channels and/or external sources (common mode signal) may be the same for each of the wires of the pair, so is reduced or rejected by the differencing. The remaining difference signal is processed in the rest of the receive beamformer channel.

The receive beamformer channel is an analog or digital receive beamformer channel. The receive beamformer channel includes a delay, phase rotator, summer, and/or filter for relatively delaying and apodizing signals from different channels and then summing the signals.

An optional filter may be included in the receive beamformer or separate from the receive beamformer. The filter provides highpass, bandpass, lowpass or spectral whitening response. The filter passes information associated with the desired frequency band, such as the fundamental transmit frequency band, a harmonic of the fundamental frequency band or any other desired frequency band. As used herein, harmonic comprises higher harmonics (e.g., second, third, ...), fractional harmonics (3/2, 5/3, ...), or subharmonics (1/2, 1/3, ...). The filter may comprise different filters for different desired frequency bands or a programmable filter. For example, the filter demodulates the signals to base band. The demodulation frequency is programmably selected in response to the fundamental center frequency or another frequency, such as a second harmonic center frequency. Signals associated with frequencies other than near the base band are removed by low pass filtering. As another example, the filter provides band pass filtering.

As an additional or alternative option, a memory, phase rotator, amplifier (e.g., multiplier) and/or summer are provided. By combining received signals responsive to different transmit events with relative phasing and/or weighting, information at desired frequencies may be isolated or enhanced relative to other frequencies.

The ultrasound transducer element system 10 is used in a transducer probe. For example, the element 12 and twisted pair 26 are provided in a transducer assembly releasably connectable with an ultrasound system. The system channel 24 is provided in the ultrasound system. Other intervening components may be provided. In alternative embodiments, part or the entire system channel is provided within the transducer assembly, such as in the connector and/or in the probe. The cables of the transducer assembly include the twisted pairs 26, but may be coaxial cables with the twisted pair 26 provided at other locations between the system channel 24 and the element 12.

Figure 4:
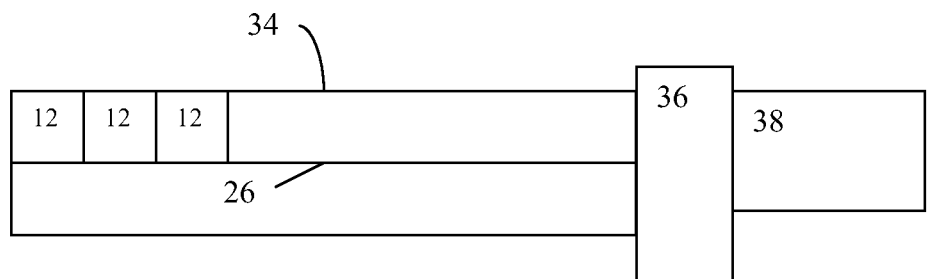
FIG. 4 is a block diagram of one embodiment of an arrangement of an array in a catheter.

In one embodiment, the ultrasound transducer element system 10 is used in a cardiac catheter, such as long (e.g., one meter), thin catheter having a diameter of 15 French or less. The element 12 and at least part of the length of the twisted pair 26 are within the catheter body. FIG. 4 shows an example catheter 34 with a plurality of elements 12 and corresponding plurality of twisted pairs 26. Using the twisted pairs 26 within the catheter body may be more space efficient than coaxial cables, allowing a smaller diameter catheter and/or greater number of elements 12.

The twisted pair 26 terminates at the connector 36 at the end of the catheter 34 or beyond the catheter outside the body. The connector 36 connects to the ultrasound system and the system channel 24. Alternatively, the connector 36 includes connectors for the twisted pair 26 and the twisted pair arrangement continues beyond the connector 36.

In one embodiment represented in FIG. 4, the connector 36 connects a disposable catheter 34 with a reusable link 38. The link 38 includes twisted pairs 26 and/or coaxial cables for releasable connection with the catheter-based ultrasound transducer assembly. Since the catheter is used in the patient, the catheter is used only once. To reduce costs, as much of the circuitry and/or components of the imaging system as possible are reused. The link 38 provides part of the cabling to connect the elements 12 of the array with the imaging system for reuse.

Where the reusable link 38 is provided, the splitter and inverter 32 and/or the differential amplifier 28 may be positioned in the ultrasound system, in the link 38, and/or in the connector 36. The remainder of the transmit and/or receive beamformer channel has similar placement or is placed within the ultrasound system to which the link 38 releasably connects. Alternatively, the differential amplifier 28 and/or inverter 32 are in the ultrasound system, and not the link 38.

Figure 5:
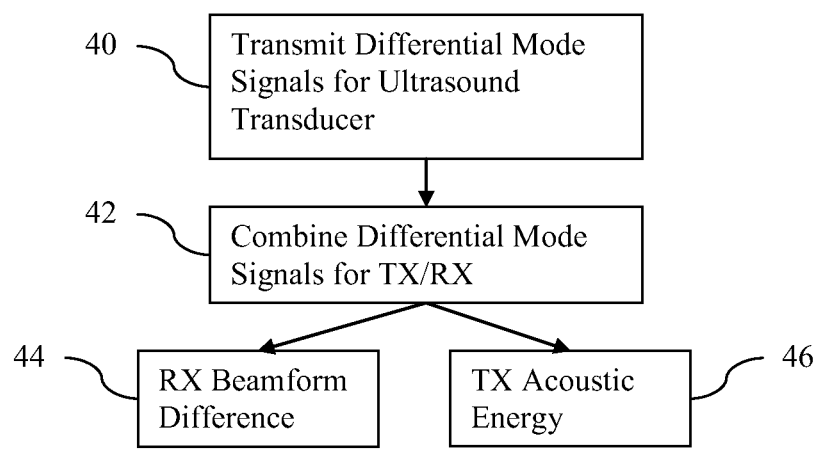
FIG. 5 is a flow chart diagram of one embodiment of a method for transmitting element signals in an ultrasound front-end.

FIG. 5 illustrates a flow chart of one embodiment of a method for noise and cross-talk reduction in ultrasound imaging. One of the embodiments of FIGS. 1-4 or a different system using twisted pairs for differential mode signals implements the method. The method is performed in the order shown or a different order. Act 46 may be performed before or after act 44. Additional, different, or fewer acts may be performed. For example, act 44 is associated with receive operation and act 46 is associated with transmit operation. Only one of acts 44 and 46 may be performed.

In act 40, differential mode signals are transmitted. The differential mode signals are transmitted for an ultrasound transducer, so are transmitted to or from the ultrasound transducer. For transmit operation, the differential mode signals are transmitted to the ultrasound transducer from a beamformer. For receive operation, the differential mode signals are transmitted from the ultrasound transducer to a beamformer.

The signals are transmitted by propagation over a twisted pair of wires. Signals with opposite polarity and the same or similar amplitude travel on wires for transmit operation. Signals generated by different layers separated by ground have different polarity and similar amplitude, so are differential mode signals propagating for receive operation.

In one example, transmit waveforms for different layers of a same element are applied to the element. The transmit waveforms are unipolar, bipolar, sinusoidal, square wave or other waveform with any number of cycles. The waveform is applied over the twisted pair by the transmit beamformer outputting the differential mode signals. The twisted pair conducts the electrical waveforms to the electrodes of the element, such as conducting the differential signals to top and bottom electrodes.

The transmit waveforms have a relatively high voltage amplitude, such as positive and/or negative 10 or more volts (e.g., 100-200 volts). Lesser or greater voltages may be used.

The transmit waveform is of a desired frequency or frequency band. For example, a center frequency of 2 MHz is provided with any size of frequency band, such as 1 or 2 MHz band. The center frequency and corresponding bandwidth are a fundamental transmit frequency and band.

In another example of transmitting differential mode signals on the twisted pair, received signals are transmitted. The waveforms for each layer are transmitted to the system separately as differential mode signals. Given opposite poling of the layers, the serial connection generates information at a harmonic band of the fundamental frequency band. Information may also or alternatively be generated at the fundamental band with poling in a same direction.

The receive waveforms have a relatively low voltage as compared to transmit waveforms. For example, the receive waveforms have an amplitude of positive and/or negative 10 or less volts. Higher or lower voltages may be used.

The higher voltage transmit waveform and lower voltage receive waveform pass along a same twisted pair, but at different times. The transmit and receive operations share the twisted pair, but separate wiring may be provided. The layers of the element are used for creating differential mode signals.

In act 42, the differential mode signals are combined. For transmit operation, the combination occurs at the element. By converting the differential mode signals to acoustic energy in different layers of a same element at a same time, the energy from both signals are combined. Common mode information may be reduced due to the combination.

For receive operation, the combination occurs electronically. A differential amplifier or other device determines a difference between the signals from the different layers. The difference is a combination. The results of the difference are used for further receive processing.

In act 46, the combined signals are used for transmitting acoustic energy. The acoustic signals generated by the different layers that do not cancel each other propagate in the patient for ultrasound imaging. In response to the differential mode signals on the electrodes with a center electrode grounded, the layers of transducer material generate acoustic energy. The different layers of transducer material contribute to the generation of acoustic energy. By having the ground separating the layers of the element, the acoustic energy constructively interferes for difference information and common mode information is reduced or eliminated.

One or more elements generate acoustic energy during a given transmit event. Using relative phasing and/or apodization between elements, a beam or beams of acoustic energy are formed.

Structure, such as tissue or fluids, reflects some of the acoustic energy back to the transducer elements. For harmonic imaging, nonlinear propagation and/or reflection generates harmonic information. Harmonic information is used for one of tissue imaging or contrast agent imaging. In tissue imaging, no additional contrast agent is added to the target during an imaging session. Only the characteristics of a tissue, including blood or other fluids, are relied on to create the ultrasonic image. Medical ultrasound imaging is typically conducted in a discrete imaging session for a given subject at a given time. For example, an imaging session can be limited to an ultrasound patient examination of a specific tissue of interest over a period of ¼ to 1 hour, though other durations are possible. In this case, no contrast agent is introduced into the tissue at any time during the imaging session. Tissue harmonic images may provide a particularly high spatial resolution as a function of the echo generated from the tissue at harmonic frequencies. In particular, there may often be less clutter in the near field. Additionally, because the transmit beam is generated using the fundamental frequencies, the transmit beam profile may be less distorted by a specific level of tissue-related phase aberration than would a transmit beam formed using signals transmitted directly at the second harmonic.

In act 44, receive beamforming is performed. Reflected acoustic energy is converted to electrical energy by the transducer elements. In response to echoes from the transmitted acoustic energy, electrical receive waveforms are generated by each transducer layer of the element. The difference signals (e.g., analog or digital) from different elements are relatively delayed and/or apodized, and then combined (e.g., summed). The result is a beamformed signal.

The beamformed signals from different transmit events and/or receive events represent a response from the patient at one or more locations. After detection, filtering and/or scan conversion, an image is generated. A B-mode, flow mode, Doppler mode, spectral Doppler, M-mode or other type of image is generated.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. An ultrasound transducer element system, the system comprising:
    at least one ultrasound transducer element comprising at least first and second layers of transducer material;
    a first electrode between the first and second layers, the electrode connected to ground for transducing;
    a second electrode adjacent the first layer and not the second layer;
    a third electrode adjacent the second layer and not the first layer;
    a twisted pair of wires where a first wire of the pair connects with the second electrode and a second wire of the pair connects with the third electrode;
    a first beamformer channel connected with the twisted pair, the first beamformer channel operable with differential mode signals corresponding to the second and third electrodes.

2. The system of claim 1 wherein the first layer is poled in a substantially opposite direction as the second layer.

3. The system of claim 1 wherein the first layer is poled in a substantially same direction as the second layer.

4. The system of claim 1 wherein the first beamformer channel comprises at least a first transmit beamformer channel connected with the twisted pair of wires, the transmit beamformer channel configured to generate the differential mode signals applied to the second and third electrodes using the first and second wires, respectively.

5. The system of claim 4 wherein the at least the first transmit beamformer channel comprises two transmit beamformer channels, each of the two transmit beamformer channels operable to provide one of the differential mode signals.

6. The system of claim 4 wherein the first transmit beamformer channel includes an inverter, the first wire connected with an output of the inverter and the second wire connected with an input to the inverter.

7. The system of claim 4 further comprising a receive beamformer channel connected with the twisted pair.

8. The system of claim 1 wherein the first beamformer channel comprises a receive beamformer channel configured to receive the differential mode signals.

9. The system of claim 8 wherein the receive beamformer channel comprises a differential amplifier having a positive input connected with the first wire and a negative input connected with the second wire.

10. The system of claim 1 wherein the transducer element and twisted pair of wires are within a catheter, the twisted pair of wires terminating at a connector link, the connector link electronically connecting the twisted pair of wires with the first beamformer channel.

11. An ultrasound transducer element system, the system comprising:
    at least one ultrasound transducer element comprising at least first and second layers of transducer material;
    a system channel configured to operate with differential mode signals; and
    a twisted pair connecting the system channel to the ultrasound transducer element wherein the ultrasound transducer element and the twisted pair are within a cardiac catheter.

12. A method for noise and cross-talk reduction in ultrasound imaging, the method comprising:
    transmitting differential mode signals between an ultrasound transducer and a beamformer; and
    combining the differential mode signals.

13. The method of claim 12 wherein transmitting comprises transmitting transmit waveforms with equal amplitude and opposite phase, and wherein combining comprises applying the transmit waveforms to different layers of the ultrasound transducer, the different layers separated by a ground connection.

14. The method of claim 12 wherein transmitting comprises transmitting receive waveforms from different layers of the ultrasound transducer, and wherein combining comprises determining a difference between the receive waveforms.

15. The method of claim 14 further comprising receive beamforming as a function of the difference.

16. The method of claim 12 wherein transmitting comprises transmitting the differential mode signals with a twisted pair of wires.

* * * * *